United States Patent [19]
Parkola

[11] Patent Number: 5,584,852
[45] Date of Patent: Dec. 17, 1996

[54] GUIDED LOCKING BALLOON PROTECTOR

[76] Inventor: Walter R. Parkola, P.O. Box 21094, El Cajon, Calif. 92021

[21] Appl. No.: 422,095

[22] Filed: Apr. 14, 1995

[51] Int. Cl.⁶ .................................................. A61M 29/00
[52] U.S. Cl. ........................... 606/194; 606/153; 604/96; 604/163
[58] Field of Search ................................ 606/192, 194, 606/195, 198, 191, 153; 604/96, 163; 24/437, 439, 441, 522; 403/326, 329

[56] References Cited

U.S. PATENT DOCUMENTS

| | | | |
|---|---|---|---|
| 4,573,981 | 3/1986 | McFarlane | 604/263 |
| 4,710,181 | 12/1987 | Fuqua | 604/280 |
| 4,738,666 | 4/1988 | Fuqua | 604/280 |
| 5,015,231 | 5/1991 | Keith et al. | 604/96 |
| 5,053,007 | 10/1991 | Euteneuer | 604/96 |
| 5,066,298 | 11/1991 | Hess | 606/194 |
| 5,137,512 | 8/1992 | Burn et al. | 604/96 |
| 5,334,160 | 8/1994 | Ellis | 604/163 |

*Primary Examiner*—Michael Powell Buiz
*Assistant Examiner*—Kevin Truong
*Attorney, Agent, or Firm*—Michael R. Shevlin; Dianne M. F. Plunkett; Harold R. Patton

[57] ABSTRACT

The present invention is for a guided locking balloon protector (10) for a dilatation catheter balloon (30) which consists of a proximal cylindrical component (15) with a distal end and a proximal end and a distal cylindrical component (20) with a distal end and a proximal end. The proximal cylindrical component (15) has two longitudinally opposed raised ribs (55) defining a slot (60) and a inner diameter (40) that can slidably fit over the balloon (25). The distal cylindrical component (20) has a inner diameter (65) that can slidably fit over balloon (25) and a integral rib (75) extending proximally from the proximal end, the integral rib (75) is sized to fit in the slot (60) and is approximately the length of the proximal cylindrical component (15). Affixed to the proximal end of the integral rib (75) is a downwardly extending locking tab (80). The method of installing the guided locking balloon protector (10) over the dilatation catheter balloon (25) includes sliding the proximal cylindrical component (15) over the distal portion (35) of the catheter (30) to cover the proximal end of the balloon (25). Next the distal cylindrical component (20) is slid over the distal portion (35) of the catheter (30) until the raised rib (75) meets the slot (60). The integral rib (75) with the locking tab (80) is inserted into the slot (60) and two components are pushed together until the proximal end of the distal cylindrical component (20) abuts the distal end of the proximal cylindrical component (15) and locking tab (80) engages the proximal end of the proximal cylindrical component (15) and locks the distal cylindrical component (20) to the proximal cylindrical component (15) covering balloon (25).

4 Claims, 3 Drawing Sheets

GUIDED LOCKING BALLOON PROTECTOR

FIELD OF THE INVENTION

This invention relates to the field of angioplasty, and more particularly to a balloon protector of a dilatation balloon catheter.

BACKGROUND OF THE INVENTION

Dilatation balloon catheters are frequently used for the treatment of stenoses in the coronary arteries. This procedure, known as percutaneous transluminal coronary angioplasty (PCTA), was developed by Dr. Andreas Gruntzig. According to this procedure, blockage in a coronary artery can be reduced by positioning a balloon dilatation catheter across the blockage and inflating the balloon, which causes stretching of the artery and pressing of the lesion into the artery wall to reestablish acceptable blood flow through the artery.

To move through the artery, the deflated balloon diameter should be as small as possible. The core or inner tube diameter of the catheter should be minimized along with the balloon, which can be done by folding, wrapping or twisting the balloon to achieve the smallest profile possible or by reducing wall thicknesses, to the extent possible, of the balloon itself. This deflated diameter affects the ease and ability of the dilatation catheter to pass through a guide catheter and through the coronary arteries leading to the stenosis to be opened.

In order to keep the outer diameter of the balloon catheter in its deflated condition, it is common to use a balloon protector. A balloon protector protects the balloon and distal tip of the catheter from possible damage during storage and keeps the balloon tightly wrapped in its deflated condition to minimize the outer diameter of the balloon in its deflated state. During the sterilization process, the catheter, with the balloon protector in place, is exposed to an elevated temperature for a period of time which causes the balloon to be heat set in the folded or wrapped configuration in which it is held by the balloon protector. This heat setting of a balloon gives the balloon a memory so that when it is inflated and deflated during an angioplasty procedure, the deflation will cause the balloon to return to its tightly wrapped heat set shape. This heat set shape will give the balloon a low profile diameter which will help when moving the catheter to a new stenosis or removal of the catheter after the procedure has been performed.

Various types and configurations of balloon protectors have been shown in the prior art, for example, in U.S. Pat. Nos. 4,738,666 and 4,710,181 to Fuqua, in U.S. Pat. No. 5,053,007 to Euteneuer, U.S. Pat. No. 5,066,298 to Hess, U.S. Pat. No. 4,573,981 to McFarlane, U.S. Pat. No. 5,015,231 to Keith et al. and U.S. Pat. No. 5,137,512 to Burns et al.

The above-noted Fuqua '666 and '181 patents propose a catheter protector comprising a hollow cylindrical sheath. The Fuqua sheath covers the entire length of the catheter, and is removed by pulling it off of the proximal end of the catheter. Fuqua also proposes providing perforations in the sheath for facilitating its removal. The above-noted Euteneuer '007 patent proposes a compression protector employing an inner sleeve applied over a deflated-balloon, an outer sleeve applied over the inner sleeve, and a compression housing for compressing the outer sleeve radially on the inner sleeve, thus compressing the inner sleeve radially on the balloon. The above-noted Hess '298 patent proposes protecting a catheter's balloon by wrapping the balloon with tape in an overlapping fashion. The above-noted McFarlane '981 patent proposes a substantially tapered cylindrical sheath which encloses a distal portion of the catheter assembly and is locked in place with two finger elements. The above noted Keith '231 patent proposes a multipart balloon protector consisting of an inner sleeve, with an elongated expansion slit to facilitate installation over the balloon, and a second outer sleeve compressing the inner sleeve. The above noted Burns '512 patent proposes a multisegment balloon protector using two protectors that cover different areas of the balloon.

SUMMARY OF THE INVENTION

There is a need for balloon protectors to protect the catheter balloons because they have become smaller, thinner, and more fragile and it has become increasingly difficult to apply a balloon protector which does not damage the balloon when installed.

Accordingly, the object of the present invention is directed to an improved balloon protector for covering and protecting the balloon of a dilatation catheter. The invention is a two piece balloon protector consisting of a proximal cylindrical component and a distal cylindrical component that are installed separately and when the proximal end of the distal cylindrical component abuts the distal end of the proximal cylindrical component, a locking tab locks them together. By using two components for the protector, each of which fits over a part of the balloon, the force required to apply each component individually is significantly less than a protector that extends over the entire length of the balloon. Having a balloon protector that can be installed in sections with less friction and twisting will lessen the risk of damage to the balloon. Once the two components are installed, they lock together to form one balloon protector and can be readily removed from the balloon prior to use.

BRIEF DESCRIPTION OF THE DRAWINGS

The foregoing and other features of the present invention will be best appreciated with reference to the following detailed description of a specific embodiment of the invention, when read in conjunction with the accompanying drawings.

DETAILED DESCRIPTION OF THE PREFERRED EMBODIMENTS

Figure 1:
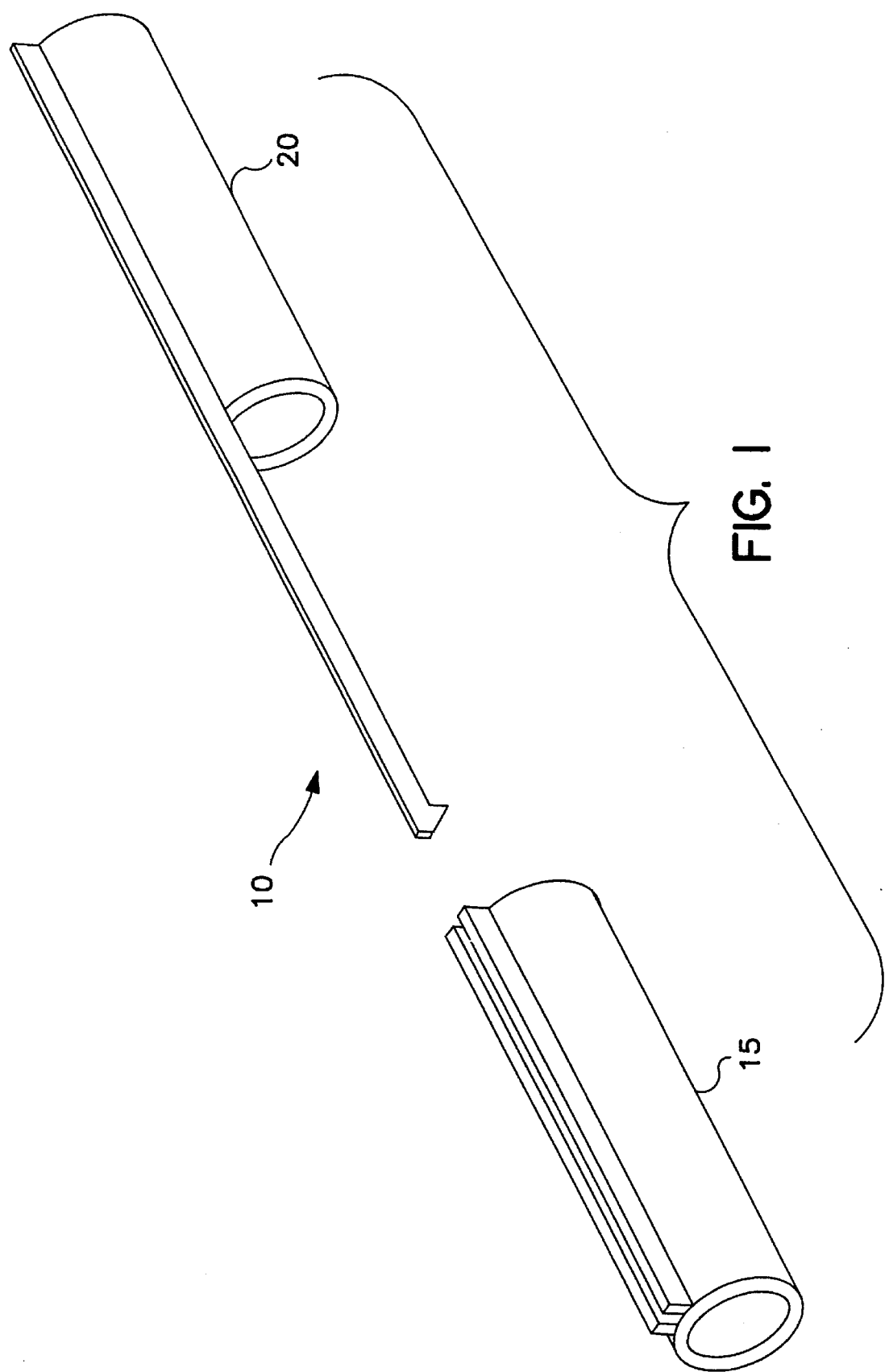
FIG. 1 is a perspective view of the guided locking balloon protector of the present invention showing the proximal and distal cylindrical components.
Figure 7:
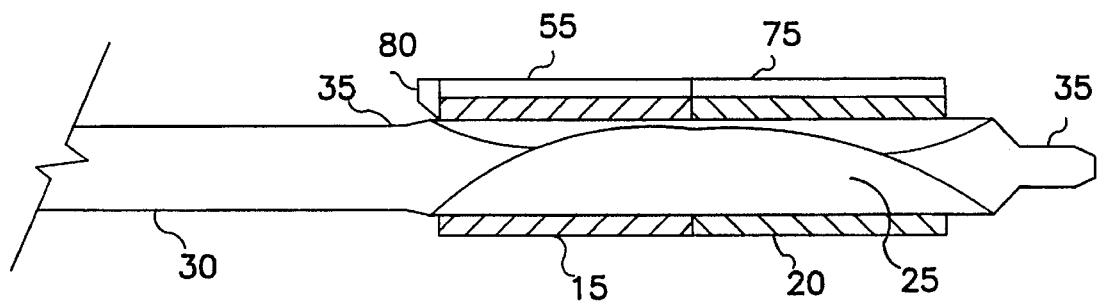
FIG. 7 is a longitudinal sectional view of the guided locking balloon protector installed on a balloon dilatation catheter.

FIG. 1 shows the present invention of a guided locking balloon protector 10 comprised of a proximal cylindrical component 15 and a distal cylindrical component 20. In the preferred embodiment, it is used as a balloon protector for the balloon 25 of a balloon catheter 30 shown with the balloon 25 and a portion of the shaft 35, as shown in FIG. 7.

Figure 2:
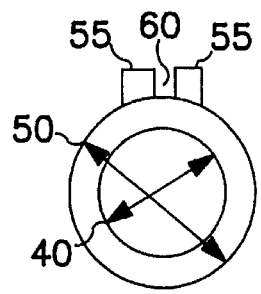
FIG. 2 is an end view of the proximal cylindrical component of the guided locking balloon protector of the present invention.
Figure 3:
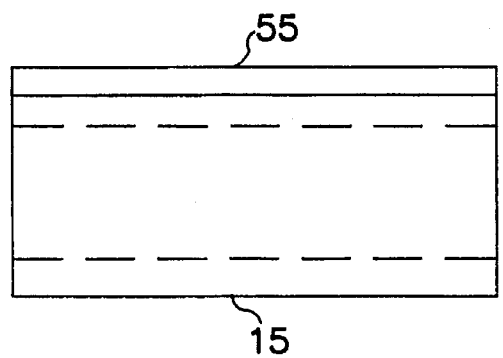
FIG. 3 is a side view of the proximal cylindrical component of the guided locking balloon protector of the present invention.

FIGS. 2 and 3 show more detail of the proximal cylindrical component 15. The proximal cylindrical component 15 is formed with an interference fit with respect to the wrapped balloon 25. The inner diameter 40 of the component is smaller than the outer diameter 45 of the wrapped balloon 25 (see FIG. 6). In the preferred embodiment, the inner diameter 40 is about 0.030 inch and the outer diameter 50 of the proximal cylindrical component is about 0.100 inch. Along the length of the proximal cylindrical component 15 are opposed raised ribs 55 that form slot 60.

Figure 4:
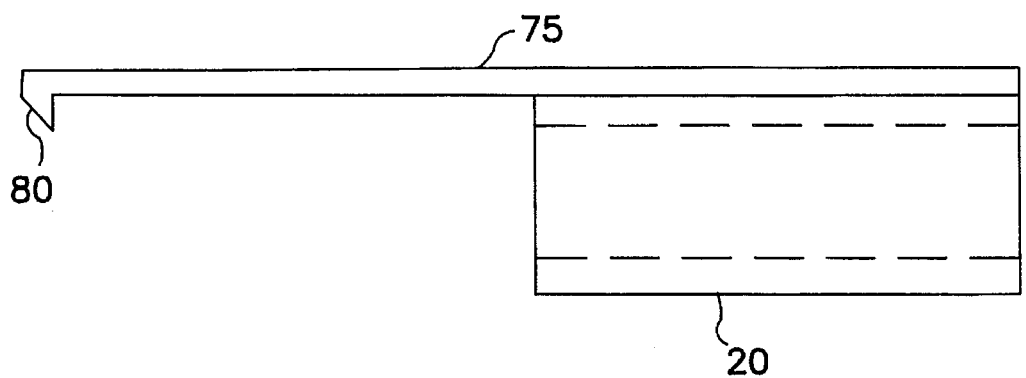
FIG. 4 is a side view of the distal cylindrical component of the guided locking balloon protector of the present invention.
Figure 5:
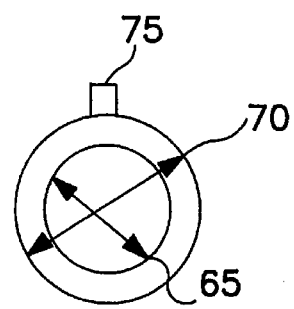
FIG. 5 is an end view of the distal cylindrical component of the guided locking balloon protector of the present invention.

FIG. 4 and 5 show more detail of the distal cylindrical component 20. The distal cylindrical component 20 is formed with an interference fit with respect to the wrapped balloon 25. The inner diameter 65 of the distal cylindrical component is smaller than the outer diameter 45 of the wrapped balloon 25 (see FIG. 6). In the preferred embodiment, the inner diameter 65 is about 0.030 inch and the outer diameter 70 of the distal cylindrical component is about 0.100 inch. Along the length of and extending beyond the proximal end of the distal cylindrical component 20 is a raised rib 75. Raised rib 75 is dimensioned to fit inside slot 60 and is approximately the length of proximal cylindrical component 15. Affixed to the proximal end of the integral rib 75 is a downwardly extending locking tab 80 located approximately the length of proximal cylindrical component 15 away from the distal cylindrical component 20. Locking tab 80 hooks over the proximal end of the proximal cylindrical component 15 to lock the proximal and distal cylindrical components together when they are joined to form the guided locking balloon protector 10.

Proximal cylindrical component 15 and distal cylindrical component 20 are preferably made of a polymeric material, such as Miles RX Polycarbonate. The inner surfaces should also have low surface friction to allow ease of installation over balloon 25. Both components could be molded from any clear sterilizable material or color coded to indicate different balloon sizes.

Figure 6:
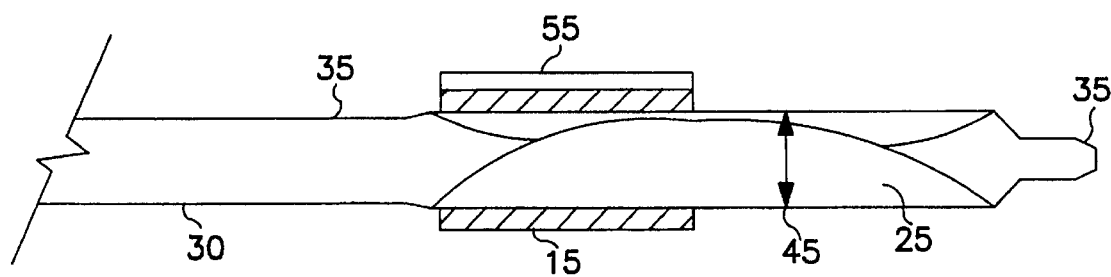
FIG. 6 is a longitudinal sectional view of the proximal cylindrical component installed on a balloon dilatation catheter.

To install the guided locking balloon protector 10, a vacuum is applied to balloon 25 to cause it to collapse to a deflated condition. As it deflates, balloon 25 wraps around shaft 35 to reduce the overall diameter of the distal portion of catheter 30. As illustrated in FIG. 6, the application of the guided locking balloon protector 10 begins by sliding the proximal cylindrical component 15 over the distal end of catheter 30 until it covers the proximal half of balloon 25. Next the distal cylindrical component 20 is aligned so that the tab 80 of the raised rib 75 is pointed toward slot 60 of the proximal component 15. As distal cylindrical component 20 is slid over balloon 25, locking tab 80 is lifted slightly so that raised rib 75 slides into slot 60. Once distal cylindrical component 20 meets proximal cylindrical component 15, tab 80 will move down and lock them together, as shown in FIG. 7. Once locked, the two components act as one and can be removed together by pushing distally on proximal cylindrical component 15. In addition, the entire length of balloon 25 can be held generally rigid during shipping and handling by the guided locking balloon protector.

Those of ordinary skill in the art will appreciate an advantageous feature of the present invention, namely, that installing the balloon protector 10 in two pieces over the dilatation catheter balloon 25 and then locking them eliminates any twisting action between the balloon protector and the balloon as other balloon protectors do. This will reduce the risk of damage to the balloon.

Although a particular embodiment of the invention has been described herein in some detail, this has been done for the purposes of illustration only and is not intended to be limiting with regard to the scope of the present invention as defined in the claims. It is contemplated that various substitutions, alterations, and/or modifications, including but not limited to those specifically discussed herein, may be made to the embodiment described herein without departing from the spirit and scope of the present invention.

| No. | Component |
| --- | --- |
| 10 | Guided Locking Balloon Protector |
| 15 | Proximal cylindrical component |
| 20 | Distal cylindrical component |
| 25 | Balloon |
| 30 | Balloon Catheter |
| 35 | Shaft |
| 40 | Inner Diameter - Proximal cylindrical component |
| 45 | Outer Diameter - Balloon |
| 50 | Outer Diameter - Proximal cylindrical component |
| 55 | Raised Rib - Proximal cylindrical component |
| 60 | Slot |
| 65 | Inner Diameter - Distal cylindrical component |
| 70 | Outer Diameter - Distal cylindrical component |
| 75 | Raised Rib - Distal cylindrical component |
| 80 | Locking Tab |

What is claimed is:

1. A guided locking balloon protector for a dilatation catheter balloon, comprising:

a dilatation catheter balloon with a proximal end and a distal end;

a proximal cylindrical component with a distal end and a proximal end with two longitudinally opposed raised ribs defining a slot and a inner diameter that can slidably fit over the proximal end of the balloon;

a distal cylindrical component with a distal end, a proximal end and a inner diameter that can slidably fit over the distal end of the balloon, an integral rib extending proximally from the proximal end of the distal cylindrical component, the integral rib is sized to fit in the slot, the integral rib is approximately the length of the proximal cylindrical component, affixed to the proximal end of the integral rib is a downwardly extending locking tab; and the locking tab engages the proximal end of the proximal cylindrical component when the proximal end of the distal cylindrical component abuts the distal end of the proximal cylindrical component and locks the distal cylindrical component and the proximal cylindrical component together, covering the dilatation catheter balloon.

2. A balloon protector in accordance with claim 1, wherein the proximal cylindrical component and the distal cylindrical component are made of polycarbonate material.

3. A balloon protector in accordance with claim 1, wherein the proximal cylindrical component and the distal cylindrical component have the same inner diameter.

4. A method of installing a guided locking balloon protector over a dilatation catheter balloon comprising the steps of:

providing a guided locking balloon protector comprising: a proximal cylindrical component with a distal end and a proximal end with two longitudinally opposed raised ribs defining a slot; a distal cylindrical component with a distal end and a proximal end with an integral rib extending proximally from the proximal end of the distal cylindrical component, the integral rib is sized to fit in the slot, the integral rib is approximately the length of the proximal cylindrical component, affixed to the proximal end of the integral rib is a downwardly extending locking tab;

providing a dilatation catheter with a balloon on the distal end;

mounting the proximal cylindrical component over the distal end of the dilatation catheter;

sliding the proximal cylindrical component proximally until it covers the proximal portion of the dilatation catheter balloon;

mounting the distal cylindrical component over the distal end of the dilatation catheter;

sliding the distal cylindrical component proximally until the raised rib with locking tab of the distal cylindrical component engages the slot of the proximal cylindrical component and inserting the raised rib into the slot; and sliding the distal cylindrical component further until the proximal end abuts the distal end of the proximal cylindrical component and the locking tab engages the proximal end of the proximal cylindrical component, locking the distal cylindrical component to the proximal cylindrical component to cover and protect the dilatation catheter balloon.

\* \* \* \* \*